United States Patent
Zijlstra et al.

(10) Patent No.: US 10,330,676 B2
(45) Date of Patent: Jun. 25, 2019

(54) PLASMONIC BIOSENSOR BASED ON MOLECULAR CONFORMATION

(71) Applicant: Technische Universiteit Eindhoven, Eindhoven (NL)

(72) Inventors: Peter Zijlstra, Utrecht (NL); Menno Willem José Prins, Rosmalen (NL)

(73) Assignee: Technische Universiteit Eindhoven, Eindhoven (NL)

(*) Notice: Subject to any disclaimer, the term of this patent is extended or adjusted under 35 U.S.C. 154(b) by 0 days.

(21) Appl. No.: 15/526,010

(22) PCT Filed: Nov. 12, 2015

(86) PCT No.: PCT/EP2015/076413
§ 371 (c)(1),
(2) Date: May 11, 2017

(87) PCT Pub. No.: WO2016/075226
PCT Pub. Date: May 19, 2016

(65) Prior Publication Data
US 2017/0328894 A1    Nov. 16, 2017

Related U.S. Application Data

(60) Provisional application No. 62/078,870, filed on Nov. 12, 2014, provisional application No. 62/092,763, filed on Dec. 16, 2014, provisional application No. 62/132,096, filed on Mar. 12, 2015.

(51) Int. Cl.
*A61K 48/00* (2006.01)
*C07H 21/02* (2006.01)
*C07H 21/04* (2006.01)
*G01N 33/543* (2006.01)
*G01N 33/542* (2006.01)
*C12Q 1/6825* (2018.01)
*G01N 21/552* (2014.01)

(52) U.S. Cl.
CPC ..... *G01N 33/54373* (2013.01); *C12Q 1/6825* (2013.01); *G01N 21/554* (2013.01); *G01N 33/542* (2013.01); *G01N 33/5436* (2013.01); *G01N 33/54346* (2013.01)

(58) Field of Classification Search
CPC .............. C12N 2310/16; C12N 15/115; A61K 2300/00
See application file for complete search history.

(56) References Cited

FOREIGN PATENT DOCUMENTS

WO    WO2013048318    4/2013

OTHER PUBLICATIONS

Sönnichsen et al., "A molecular ruler based on plasmon coupling of single gold and silver nanoparticles," Nat. Biotechnol. 23, 741-745 (2005).
Xu et al., "Switchable nanodumbbell probes for analyte detection," Small vol. 9, No. 2, 228-32 (2013), abstract only.
Reinhard, et al., "Use of plasmon coupling to reveal the dynamics of DNA bending and cleavage by single EcoRV restriction enzymes," Proc. Natl. Acad. Sci. U. S. A. 104, 2667-72 (2007).
Zhao et al. Exciton-Plasmon Interactions between CdS Quantum Dots and Ag Nanoparticles in Photoelectrochemical System and Its Biosensing Application. Anal. Chem., 2012, 84(14)5892-5897 DOI:10.1021/ac300127s.
Deng et al. An off-on-off electrochemiluminescence approach for ultrasensitive detection of thrombin. Biosens Bioelectron. Sep. 15, 2014;59:58-63. doi: 10.1016/j.bios.2014.03.012. Epub Mar. 15, 2014.
Balamurugan et al. Nanostructure shape effects on response of plasmonic aptamer sensors. J Mol Recognit 26 (9), 402-407. Sep. 2013.
Li et al. Fluorescence quenching of quantum dots by gold nanorods and its application to DNA detection. Applied Physics Letters 94, 063111 (2009); doi: 10.1063/1.3080662. View online: http://dx.doi.org/10.1063/1.3080662.
Slavik et al. Ultrahigh resolution long range surface plasmon-based sensor. Sensors and Actuators B 123 (2007) 10-12. DOI: 10.1016/j.snb.2006.08.020.
Baaske et al. Single-molecule nucleic acid interactions monitored on a label-free microcavity biosensor platform. Nature Nanotechnology 9, 933-939 (2014) doi:10.1038/nnano.2014.180.
Morimura et al. Nano-Analysis of DNA Confirmation Changes Induced by Transcription Factor Complex Binding Using Plasmonic Nandimers.

Primary Examiner — Amy H Bowman
(74) Attorney, Agent, or Firm — Lumen Patent Firm (57) ABSTRACT

A target analyte in a matrix is sensed using a sensor device having protrusions [500] such as e.g. nanorods, containing free charge carriers. Conformational molecules [504, 506] are bound at a first end to the protrusions, and bound at a second end to a label [502] e.g. a nanoparticle, that is free to move relative to the protrusions. The conformational molecule changes its conformation when bound to the analyte, thereby changing the distance and/or the relative orientation of the label to the protrusion. Energy [510] is used to excite free electrons in the protrusion near a plasmon resonance and resulting optical radiation [514] at wavelengths near the plasmon resonance wavelength is detected [516] and analyzed [518] to determined the presence/concentration of the analyte.

9 Claims, 7 Drawing Sheets

PLASMONIC BIOSENSOR BASED ON MOLECULAR CONFORMATION

CROSS-REFERENCE TO RELATED APPLICATIONS

This application is a 371 of PCT/EP2015/076413 filed on Nov. 12, 2015. PCT/EP2015/076413 filed on Nov. 12, 2015 claims the benefit of U.S. Provisional Applications 62/078,870 filed on Nov. 12, 2014, 62/092,763 filed on Dec. 16, 2014 and 62/132,096 filed on Mar. 12, 2015

FIELD OF THE INVENTION

The present invention relates generally to biochemical detection and monitoring. More particularly, the invention relates to a biosensing device for the detection of analytes.

BACKGROUND OF THE INVENTION

Most biosensing principles for biochemical markers have been developed for use in in-vitro diagnostics, where a sample is taken (e.g., blood or saliva) and is transferred to an artificial device (e.g., a plastic disposable) outside a living organism. In such biosensing assays, a wide range of sample pre-treatment steps can be applied (e.g., separation or dilution steps) and multiple reagents can be introduced in the assay (e.g., for target amplification, signal amplification, or washing steps), often resulting in waste materials. Examples of in-vitro biosensing assays are: immunoassays, nucleic acid tests, tests for electrolytes and metabolites, electrochemical assays, enzyme activity assays, cell-based assays, etc.

In in-vivo biochemical sensing, at least a part of the sensor system remains connected to or is inserted in the human body, e.g., on the skin, or in the skin, or below the skin, or on or in or below another part of the body. Due to the contact between the biosensor and the living organism, in-vivo biochemical sensing sets high requirements on biocompatibility (e.g., inflammation processes should be minimized) and the sensor system should operate reliably within the complex environment of the living organism. For monitoring applications, the system should be able to perform more than one measurement over time and the system should be robust and easy to wear.

An important application of in-vivo biochemical sensing is continuous glucose monitoring (CGM). A disadvantage of present-day CGM systems is that the sensor response shows drift, and therefore the systems require regular recalibration by an in-vitro blood glucose test. Continuous glucose monitoring is generally based on enzymatic electrochemical sensing. Current sensors show drift and need regular recalibration. Single-molecule sensitivity is not achieved.

SUMMARY OF THE INVENTION

The current invention is a new biosensing technology for in-vivo biochemical monitoring, where the sensing principle is designed to be sensitive, specific, stable, and biocompatible. The invention is also relevant for in-vitro diagnostic testing, particularly for point-of-care testing, where it is advantageous if a specific molecular binding process leads to a signal that is detectable without further chemical/biochemical/fluidic processing. The current invention provides a reliable and easy to use biochemical monitoring and detection technique that is suitable, for example, for continuous glucose monitoring, which is very relevant for diabetic patients; electrolyte and metabolite monitoring, which is relevant for patients that may become unstable, e.g., in critical care; electrolyte measurements, which are helpful to monitor kidney function, e.g., in cardiac patients; protein measurements, which can be helpful to monitor, e.g., cardiac function (e.g., BNP as an important marker for heart failure) or inflammation; drug and/or drug metabolite measurements, which are helpful to monitor drug intake (compliance) and pharmacokinetics (aiming to keep the drug within the desired concentration window); or drug response measurements, which is helpful to monitor drug effectiveness.

The current invention provides advantages that include stability in that there is no bleaching and no blinking, and reliability/specificity, where the plasmon field relies on free charge carriers (e.g., electrons), which are present in high numbers. Therefore the plasmonic transduction principle is quite insensitive to the chemical conditions of the fluid.

The invention allows for the real-time probing of analyte concentrations in complex fluids (e.g., blood, saliva, interstitial skin fluid). Single-molecule resolution is achievable for high sensitivity. Furthermore, high specificity can be reached by isolating specific from non-specific interactions by performing signal processing on collected data, e.g., on a molecule-by-molecule basis. This allows direct real-time series of measurements in complex fluids without repeated sample taking or intermediate filtering steps.

The current invention is useful for in-vivo biosensing and for in-vitro biosensing, where the biosensors are based on particle labels and can have single-particle and single-molecule resolution. The current invention may also find application in biological, biomedical and pharmaceutical research, e.g. to monitor assays with live cells, tissue, organs, etc.

Applications of the current invention that would benefit from a reliable and easy to use biochemical monitoring system include continuous glucose monitoring for diabetic patients, without the need to regularly recalibrate the sensor system, electrolyte and metabolite monitoring, which is important for patients that may become unstable, e.g., in critical care for patient monitoring systems; electrolyte measurements for monitoring kidney function, for example in cardiac patients; protein measurements for monitoring cardiac function (for example BNP is a key marker for heart failure) or inflammation; drug and/or drug metabolite measurements are helpful to monitor drug intake, such as for compliance, and pharmacokinetics directed to keeping the drug within the desired concentration window; and drug response measurements for monitoring drug effectiveness. Analytes can be electrolytes, small molecules, lipids, carbohydrates, peptides, hormones, proteins, oligonucleotides, DNA, RNA, etc.

In one aspect, the present invention provides a method for sensing an analyte. The method includes bringing a matrix containing the analyte into contact with a sensor device having protrusions containing free charge carriers. Conformational molecules are bound at a first end to the protrusions, and bound at a second end to a label, where the label and protrusion can move with respect to each other. In some embodiments, the protrusion is static and the label is mobile. In other embodiments, the protrusion is mobile and the label is static. The conformational molecule changes its conformation and/or size and/or shape and/or orientation, when bound to the analyte, thereby changing the distance and/or the relative orientation of the label to the protrusion. The method includes exciting free charge carriers (e.g., electrons) in the protrusion and detecting optical radiation at wavelengths from the protrusions, where the exciting and/or detecting is performed at a wavelength near the plasmon resonance wavelength of the protrusion while the matrix containing the analyte is in contact with the protrusions of the sensor device. The presence/concentration of the analyte is determined from changes in the detected optical radiation while the matrix containing the analyte is in contact with the protrusions of the sensor device.

In some embodiments, bringing the analyte into contact with the protrusions of the sensor device comprises bringing a fluid containing the analyte or an analyte-permeable matrix containing the analyte into contact with the protrusions of the sensor device.

In some embodiments, the protrusions have a long axis that is smaller than 200 nm, and at least one short axis that has a length that is shorter than 80% of the long axis. Alternatively, the protrusions have a cross-sectional area of which the long axis is smaller than 200 nm while the height that protrudes out of the cross-sectional area is at least 0.75 times the long axis of the cross-sectional area.

In some embodiments, the protrusions are non-spherical metallic particles, e.g., nanorods or bipyramids.

In another aspect, the invention provides a system for sensing an analyte. The system includes a sensing device that includes at least two objects connected by at least one conformation-modulation molecule (CMM). The CMM is attached to a protrusion of at least one of the two objects. The CMM is selected such that the binding of at least one target analyte to the CMM changes the molecular conformation of the CMM, and thereby changes the distance between the at least two objects and/or the relative orientation of the at least two objects. The protrusion is a convex structure that has in two dimensions a radius of curvature of less than 100 nm, such that the protrusion may generate a localized electromagnetic field when excited.

In another aspect, the protrusion contains free electrons that may be excited near a plasmon resonance, for example by optical or electrical excitation. Detection of changes of distance and/or relative orientation can occur via excitation and/or detection near the plasmon wavelength of the protrusion. For example, plasmon excitation can occur by irradiating with light at a wavelength near the plasmon wavelength, and detection can occur also near the plasmon wavelength. Alternatively, plasmons can be excited by electrical means and light can be detected near the plasmon wavelength. Or optical excitation can occur near the plasmon wavelength and optical detection can occur away from the plasmon wavelength, e.g., when using two-photon luminescence, 2nd harmonic generation, or higher order techniques. Or optical excitation can occur away from the plasmon wavelength and optical detection near the plasmon wavelength, e.g., in case of one-photon luminescence with excitation at short wavelengths and detection near the plasmon.

The system includes a detector that is capable of detecting optical radiation, such as elastic or inelastic emission effects from the excited plasmons. The system also includes a processor for determining the presence and/or concentration of the target analyte from changes of plasmon resonance properties indicated by the detected optical radiation.

The detector may be realized as a camera with sufficient dynamic range and wavelength sensitivity to achieve single-molecule resolution. In a further embodiment, the system may include an optical probe (e.g., optical fibre) to allow for measurements to be conducted directly in complex biological environments.

In some embodiments, at least one of the two objects is a plasmonic nanorod, e.g., containing silver or gold. In some embodiments, at least one of the two objects is anchored to a body that has a dimension that is larger than the largest dimension of the at least two objects such as a surface, a matrix, a scaffold, a network, or a polymer. In another aspect, the nanoparticles are embedded in a matrix that has a filtering function such as being open for target analyte.

According to a further aspect of the invention, the CMM may be a natural, semi-synthetic, or synthetic molecule or a molecular construct with modular buildup, containing a member of one of the following classes of molecules: (bio)polymers, aptamers, nucleic acids, peptides, carbohydrates, or proteins.

In another aspect of the invention, at least one of the two objects may have a size on a nanometer scale, for low viscous drag, for high speed, for rapid measurement of conformation changes, in order to record binding/unbinding events with single-molecule resolution, and in order to increase specificity. Low viscous drag and rapid measurements will be particularly useful if the affinity between the CMM and the analyte is low. In that case the CMM undergoes short and rapid conformational changes, which can only be resolved if one of the objects is of nanometer dimensions and can follow conformational change without being slowed by drag.

In yet another aspect of the invention, the processor may perform histogram and/or histogram processing (e.g., filtering) to suppress background noise and enhance specificity. For example, short-lived events (that are dominantly weak and non-specific interactions), and long-lived events (that are dominantly specific interactions), can be discriminated on a molecule-by-molecule basis. This increases sensing specificity and allows for the continuous measurement of analyte concentrations in very complex environments, such as in-vivo or directly in body fluids such as blood.

In yet another aspect of the invention, multiple objects connected by a CMM are detected and monitored in parallel. This increases the statistics and allows for multiplexed measurements (e.g., multiple objects, multiple object types, multiple CMM types). E.g., controls can be included, and data can be collected for multiple analyte types.

According to another aspect of the invention, the analyte is a member of one of the following classes of molecules: electrolytes, metabolites, small molecules, drugs, peptides, proteins, hormones, or nucleic acids.

DETAILED DESCRIPTION

Upon irradiation with light, the free conduction electrons of metallic nanostructures oscillate collectively, known as surface plasmon, because of its interaction with the light's electric field, with a resonant frequency that depends on the nanoparticles' size, shape, and composition. When the resonance conditions are met, the incident photon resonates with the surface plasmon, which leads to the absorbance and scattering of the incident light. Resonance and, hence, the wavelength of absorption depends on the nature of the metal, size of the nanostructure, its aspect ratio and the local dielectric environment around the nanostructure, which can be summed as the refractive index of the surrounding medium. For example, 13-nm gold nanoparticles show one absorption band in water at 520 nm. Other metallic nanostructures such as gold and silver nanorods and other shapes show two peaks, one peak due to resonance between lateral modes with light and one for resonance due to the longitudinal modes that is tunable from the visible through the near infrared, depending on the nanorod aspect ratio.

Like surface plasmon resonance (SPR), localized surface plasmon resonance (LSPR) can measure the changes in the local refractive index, which results in the concomitant shift in the wavelength peak in the extinction spectra. Unlike SPR, LSPR has a higher sensitivity to refractive index changes very close to the surface, within a range of 5-15 nm from the nanostructure surface, compared with approximately 200-300 nm from metal film surface in SPR. In both cases, the sensitivity decreases exponentially from the surface. Thus, the sensitivity of a LSPR biosensor can be increased by using a small bioreceptor near the surface. The present inventors have discovered a technique for increasing sensitivity through the use of a label attached to a biomolecule, such as aptamers, that undergoes a large conformational change when a target molecule binds to it.

Aptamers are oligonucleotides that are specifically selected to bind to its target molecules by an in vitro combinatorial process called SELEX, Systematic Evolution of Ligands by Exponential Enrichment. Aptamers are either RNA or DNA and normally contains 15-60 nucleotide sequences. Aptamers show high affinity and selectivity that is traditionally associated with proteins such as antibodies. These artificial antibodies are small compared with antibodies and can immobilize directly on the gold nanostructures via end functional group in a particular orientation using a number of bioconjugation routes. These small receptors increase the sensitivity of the LSPR compared with antibody-based LSPR sensors by binding the target close to the gold surface.

Aptamers or other similar biomolecules immobilized on the surfaces of gold nanorod and gold bipyramid nanostructures allow LSPR sensing of target analyte with significant increase in sensitivity. Because of the compact structure of such biomolecules, capture of the target protein is positioned optimally for maximum LSPR signal affording detection of e.g. picomolar concentrations of target analytes.

Figure 1A:
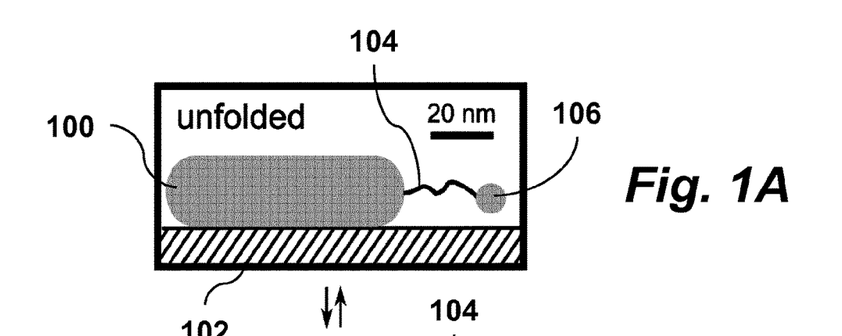
FIGS. 1A and 1B are schematic diagrams of a sensing device showing unfolded and folded states, respectively, according to an embodiment of the invention.
Figure 1B:
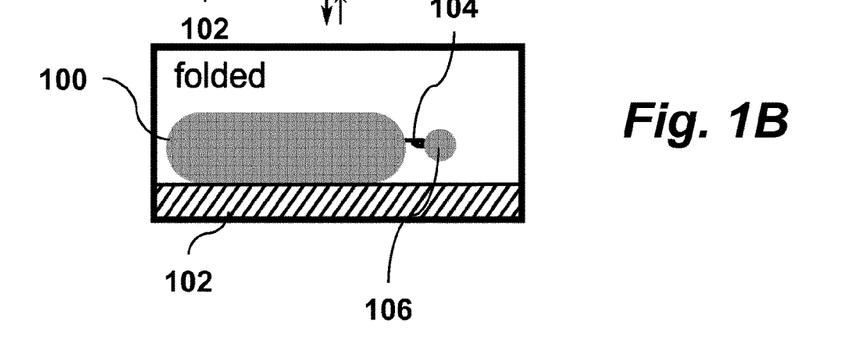
Figure 1C:
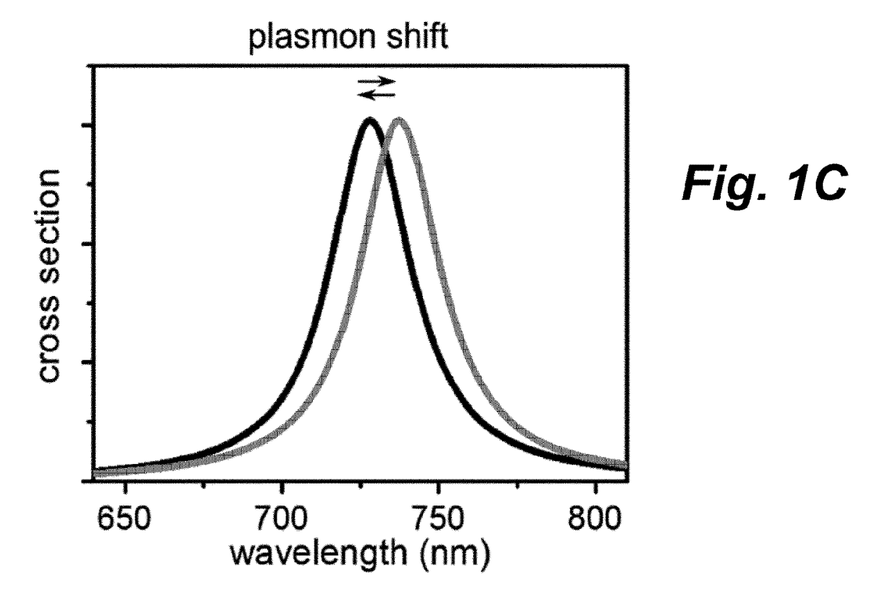
FIG. 1C is a graph of scattering cross-section vs wavelength for unfolded and folded states of a sensing device, showing a detected shift in wavelength of a plasmon resonance peak, according to an embodiment of the present invention.

FIGS. 1A and 1B are schematic diagrams of a sensing device according to an embodiment of the invention. The sensing device includes a protrusion 100 which may be attached to a substrate 102. A conformation modulation molecule (CMM) 104 is bound at a first end to the protrusion, and bound at a second end to a label 106 whose motion is constrained by the state of the conformational molecule but is otherwise free to move relative to the protrusion. The conformational molecule 104 changes its conformation when bound to a target analyte, thereby changing the distance and/or the relative orientation of the label 104 to the protrusion 100. FIG. 1A shows the unfolded state of the CMM when the analyte is not present, while FIG. 1B shows the folded state of the CMM when the analyte is present. The protrusion 100 has free electrons which may be excited near a plasmon resonance while the matrix containing the analyte is in contact with the protrusions of the sensor device. The conformation change of the CMM in response to the presence of the analyte thus modulates the inter-particle distance, resulting in a change of the plasmon resonance (e.g., a color change or a spectral shift) which may be detected optically or electrically. FIG. 1C is a graph of the detected shift in wavelength of a plasmon resonance peak. In a preferred embodiment, the protrusion is a gold nanorod. The narrow line width and bright optical response of a single gold nanorod enables high sensitivity, e.g., single-molecule sensitivity.

FIGS. 1A and 1B show an embodiment in which a nanorod with protrusion 100 is attached to a substrate 102 and where label 106 is free to move, so that the label and the protrusion can move with respect to each other. Alternatively, the label can be attached to a substrate and the nanorod with protrusion can be free to move, allowing the label and the protrusion to move with respect to each other. For example, a gold nanosphere label is attached to a glass substrate, and the nanorod is free to move in solution with respect to the label, with a motion that is restricted by the CMM. The function of the label is to alter the plasmon resonance in the nanorod, in dependence of the relative position of the label with respect to the nanorod. Alternatively, a substrate can act as a label, e.g., a nanorod is attached to a substrate via a CMM, and a change of the CMM causes a change of proximity of the nanorod to the substrate. The change of proximity to the substrate causes a change of the plasmon resonance of the nanorod. The change of plasmon resonance is detected and serves to determine the presence/concentration of the analyte from changes in the detected optical signal.

According to one embodiment, the protrusion 100 is preferably a convex structure that has, in two dimensions, a radius of curvature of less than 100 nm, where the protrusion is capable of producing a localized electromagnetic field when it is excited, such that only a small volume of fluid or matrix near the protrusion is exposed to the electromagnetic field. Free electrons in the protrusion are excited near a plasmon resonance by optical or electrical excitation. The plasmons excited in the protrusion may be detected by optical radiation, which can include elastic or inelastic effects. The localized electromagnetic field causes a high sensitivity of the plasmon to inter-object distance and/or orientation. The presence and/or concentration of the target analyte is then detected by the change of plasmon resonance properties of the device.

In one embodiment, the protrusion 100 is a gold nanorod with a small (less than 100 nm) radius of curvature at its tip.

The spectral breadth of the nanorod is 3-5 fold narrower compared to commonly used spherical particles. Moreover, their brightness and their plasmon shift (i.e., color changes) are more than ten times larger compared to a sphere of equal volume. This narrow spectral line width combined with increased sensitivity enables the detection of the binding of a single target molecule to the CMM, i.e., single-particle sensitivity. These changes in color can be detected in an optical setup with wavelength sensitivity.

In one embodiment, the target 106 is a metal (e.g., silver or gold) nanoparticle that strongly absorbs a certain part of the optical spectrum due to its plasmon resonance. The plasmon resonance changes when the distance and/or orientation of the particle with respect to the surface protrusion 100 changes. The metal nanoparticles, for example, may be made of gold, which strongly absorbs a certain part of the optical spectrum due to its plasmon resonance, where it has a strong absorption peak as a specific wavelength, or color. This color peak changes its wavelength when the distance between the target and protrusion change by as little as 10 nm, depending on the size of the particles. The target size is preferably on a nanometer scale, for low viscous drag, for high speed, for rapid measurement of conformation changes, in order to record binding/unbinding events with single-molecule resolution, and in order to increase specificity. Low viscous drag and rapid measurements will be particularly useful if the affinity between the CMM and the analyte is low. In that case the CMM undergoes short and rapid conformational changes, which can only be resolved if one of the objects is of nanometer dimensions and can follow conformational change without being slowed by drag.

The CMM 104 may be an aptamer or other biomolecule that undergoes a large conformational change when a target molecule binds. The CMM 104 binds the protrusion 100 and target 106 to form a dimer. The CMM is preferably a natural, semi-synthetic, or synthetic molecule, such as a member of one of the following classes of molecules: (bio)polymers, aptamers, nucleic acids, peptides, or proteins.

The protrusion 100 is preferably anchored to a body 102 that has a dimension that is larger than the largest dimension of the dimer. The body may be a substrate, a matrix, a scaffold, a network, or a polymer. In another aspect, the protrusion and target may be embedded in a matrix that has a filtering function such as being permeable to the target analyte.

In some embodiments, multiple targets 106 may be connected by multiple CMMs 104 to multiple protrusions 100, allowing detection at many sites in parallel. This increases the statistics and allows for multiplexed measurements. These may include multiple distinct types of CCMs, targets, and protrusions, designed for detection of distinct analytes. Controls can be included, and data can be collected for multiple analyte types. The analytes may be a member of one of the following classes of molecules: electrolytes, metabolites, small molecules, drugs, peptides, proteins, hormones, or nucleic acids. Analytes can be measured directly, i.e., by binding directly to the CMM. Alternatively, the analyte can be measured indirectly, e.g., by being converted (e.g., by an enzyme) into a product that then binds to the CMM. Yet alternatively, the analyte can be measured indirectly by a competitive process, e.g., by competing with an analyte-analogue for binding to the CMM. Thus, in the present description, when referring to an analyte that binds to the CMM, this can refer to the analyte product or analyte analogue that serves as an indirect indicator of the target analyte.

An optical or electrical detector may be coupled with the sensing device of FIGS. 1A-B to detect changes in the plasmon resonance peak. A processor connected to the detector may then process the detected changes to determine the presence of the analyte. In one embodiment, histogram and/or histogram processing (e.g., filtering) are used to suppress background noise and enhance specificity. For example, short-lived events (that are dominantly weak and non-specific interactions), and long-lived events (that are dominantly specific interactions), can be discriminated on a molecule-by-molecule basis. This increases sensing specificity and allows for the continuous measurement of analyte concentrations in very complex environments, such as in-vivo or directly in body fluids such as blood.

The sensing device of FIGS. 1A-B may be used as a component of a system for detecting analytes. According to one embodiment of the invention, such a system is connected in a closed-loop with a treatment system such as a device that doses a drug, such as insulin in the case of diabetes, or a device that otherwise influences the body, for example a device that provides an organ with a physical stimulation, such as electrical. More generally, the sensing device may be used for in-vivo, ex-vivo, or in-vitro applications. It may be used for applications on human subjects, or on non-human subjects, e.g., in veterinary applications or for testing of other biological systems.

The sensing device may be part of a disposable probe that is in contact with the subject or with the biological system, or it may be part of a disposable cartridge, e.g., a lab-on-a-chip cartridge. Such a probe or cartridge may be attached to an instrument or an analyzer in order to power and/or actuate and/or read out the probe or cartridge. Such an instrument is suited for processing signals from the probe or cartridge, and/or for communicating data between the instrument and the probe or cartridge, and/or for communicating data between the instrument and e.g., an information system or communication network.

Sensor devices according to some embodiments of the invention may be fabricated as follows. A localized surface plasmon resonance (LSPR) sensor surface may be fabricated by the deposition of gold nanorods on a glass substrate and subsequent immobilization of the DNA aptamer, which specifically bind to thrombin. This LSPR aptamer sensor has a response of 6-nm wavelength shift for protein binding with the detection limit of at least 10 pM.

A LSPR sensor may also be fabricated using gold bipyramid, which has higher refractive index sensitivity than the gold nanorods, but the overall response of gold bipyramid sensor appears to be 25% less than that of the gold nanorod substrate, despite the approximately twofold higher refractive index sensitivity. This is due to the low surface density of aptamers on the gold bipyramid compared with gold nanorods. The small size of aptamers relative to other bioreceptors is the key to achieving high sensitivity by biosensors on the basis of LSPR.

Gold nanorods may be grown from a gold nanoparticle seed solution prepared using sodium borohydride reduction of hydrogen tetrachloroaurate (III) in the presence of the surfactant CTAB. This seed solution is added to a nanorod growth solution consisting of 425 ml of 100 mM CTAB, 18 ml of 10 mM hydrogen tetrachloroaurate (III), 2.7 ml of 10 mM silver nitrate, and 2.9 ml of 100 mM ascorbic acid.

The gold bipyramid may be prepared using sodium citrate-stabilized gold seed particles. Bipyramids are grown using 0.5 ml of 10 mM hydrogen tetrachloroaurate (III) and 10 ml of 100 mM CTAB mixed with 0.1 ml of 10 mM silver nitrate solution. Sequentially, 0.2 ml of 1.0M HCl and 0.08 ml of 100 mM ascorbic acid are added to the solution, and the seed solution is added. The volume of seed solution is varied between 15 and 50 ml to synthesize different sizes of gold bipyramids. These solutions are kept at 28 C for several hours. During this time, the color changes gradually from almost clear to dark pink, with most of the color change occurring in the first hour.

The gold nanorods are deposited on the clean glass microscopic slide. First, the clean glass slides were immersed overnight in a 5-mM APTES solution in ethanol, rinsed with water, and dried under the flow of dry nitrogen. The APTES coated glass slides are then immersed in a PEGylated nanorod solution overnight. Then, the slides are rinsed and dried, and a uniform layer of gold nanorods remained on the surface with an absorbance of approximately 0.1 at the LSPR peak wavelength. The gold bipyramid substrates are also prepared using the same procedure. The CTAB-stabilized gold nanostructures (nanorods and bipyramids) were PEGylated by suspension in thiolated PEG solution for 12 hr.

Glass substrates coated with gold nanorod as well as gold bipyramid are subjected to an oxygen plasma cleaner at low power for 30 sec in 200 mT oxygen then rinsed with ethanol, water and briefly dried in a stream of dry nitrogen. The cleaned LSPR substrates are immersed in 1 mM solutions of an aptamer thiol solution in 1 M potassium phosphate solution (pH 8) for 2 hr, then rinsed with deionized water and briefly dried in a stream of dry nitrogen. Immersion of these substrates in 10 mM of $HS(CH_2)_{11}(OCH_2CH_2)_3OH$ (EG3-OH) solution in ethanol for 2 hr, rinsing with ethanol and then water, and drying in a stream of dry nitrogen covers the remaining bare gold with EG3-OH.

Figure 2:
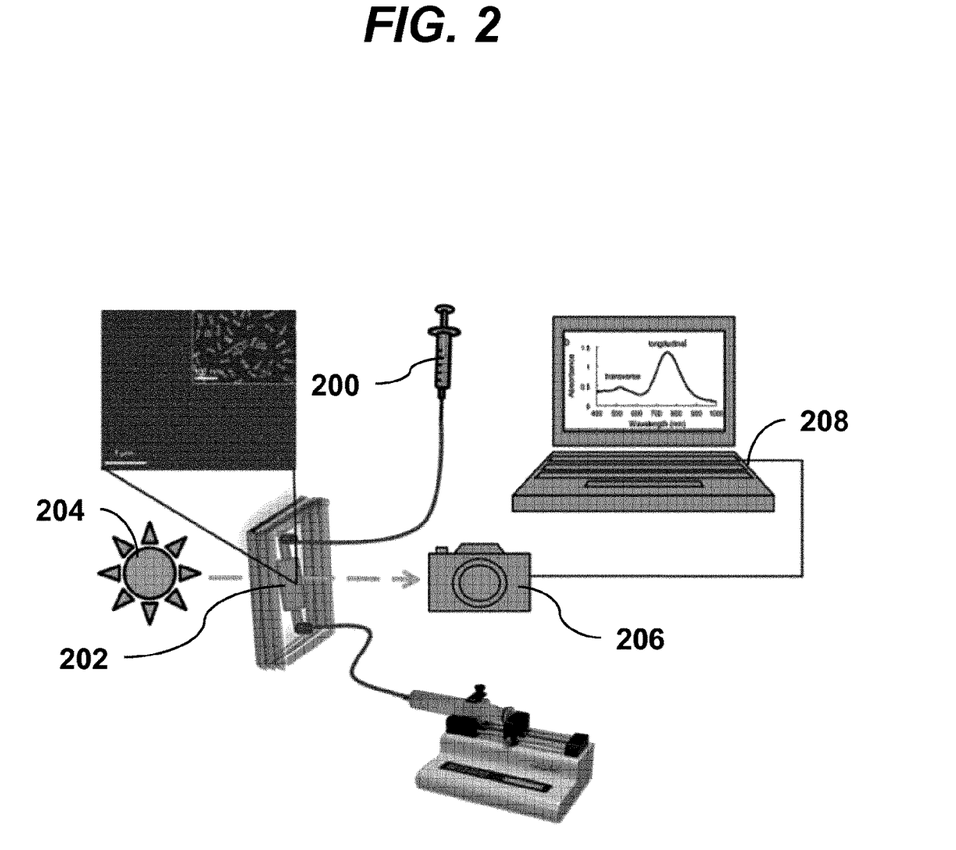
FIG. 2 is a schematic diagram of system for sensing an analyte in a fluid, according to an embodiment of the present invention.

An analyte may be sensed in a fluid using a system as shown in FIG. 2. A fluid containing an unknown quantity of a target analyte is provided in vessel 200 from which it flows through sensing device 202 in the form of a closed flow cell. An interior wall of the cell 202 is a substrate with protrusion, CMM, and label, as described above in relation to FIGS. 1A-B. In one specific realization, a glass slide is coated with gold nanorod substrate and functionalized with mixed aptamer monolayer on one side and a clean glass slide on the other side separated with a 1.5-mm-thick polydimethylsiloxane (PDMS). Two holes are drilled to connect the input and output flows of fluid through the cell, and the PDMS sheet provides a 1 cm 2 cm slot that serves as the flow volume.

This flow cell 202 is mounted vertically on an optical bench in between a quartz-tungsten-halogen light source 204 with collimating lens and a portable spectrometer 206. A flow rate of 400 ml/min is controlled by a syringe pump. After equilibration with PBS buffer, the fluid with target analyte passes over the sensor device surface under flow conditions. Absorbance spectra are collected continuously with averaging every 30 sec and recorded. Each spectrum is then analyzed by processor 208 to monitor the peak wavelength, height, and width versus time.

The utility of aptamers for LSPR applications is amplified by the high sensitivity to protein binding, which can be attributed to the relatively compact size of the aptamer. Thus, the integration of aptamers into LSPR sensors can provide the highest sensitivity achievable by a plasmon-based biosensor and the detection limits with a wider range of analyte concentrations versus gold nanoparticle aggregation assays. An equally appealing aspect of LSPR-based sensors is that detection is carried out by measurements using a basic hand-held UV-vis spectrophotometer, versus the high cost of equipment and supplies normally associated with SPR. Although SPR spectroscopy provides much higher sensitivity to changes in the bulk refractive index than LSPR spectroscopy, the response of the two techniques becomes comparable when measuring short-range changes in the refractive index due to a molecular adsorption layer. This is a result of the much smaller sensing volume presented by LSPR sensors, because the EM-field-decay length is 40-50 times shorter than that of the SPR sensors. Hence, the sensitivity of LSPR is comparable to SPR for the detection of adsorbed molecules in a 5-15-nm region above the substrate surface. Because of its low detection volume, LSPR measurement is not very sensitive to temperature changes as is the case with SPR. Thus, biosensors based on an LSPR format like the one described here can be used at varying ambient temperatures usually found in laboratory, hospital, or field settings.

Biopolymers such as proteins and nucleic acids fold into a three-dimensional structure within microseconds. The probing of these transition paths on single molecules remains a formidable challenge due to the photophysics (blinking, bleaching) of fluorescent labels. Embodiments of the present invention employ a new approach to probe conformational dynamics based on the detection of plasmon shifts caused by the distance-dependent coupling between two objects, e.g., gold nanorod and gold nanosphere. The large optical cross section of a plasmonic nanoparticle enables microsecond integration times, whereas the photostability allows us to detect many conformational changes of the same molecule.

Of particular interest is the folding of single aptamers, i.e., single-stranded oligonucleotides that fold into a compact conformation in the presence of a target. The conformational behavior of aptamers is readily extended to proteins and other biomolecules. The transition path time (i.e., the folding "speed") of aptamers is 10-100 µs.

Proteins are the biological workhorses that carry out vital functions in every cell. To carry out their task, proteins fold into complex three-dimensional conformations. Once folded, their intrinsic flexibility allows them to dynamically change their conformation in response to temperature, pH, ionic strength, or ligand-binding.

Recent fluorescence measurements estimate of the transition path time of ~10 µs for a small protein. However, averaging over several hundred single-molecule trajectories was required to overcome the limited brightness and photostability of the fluorophores. Conformational dynamics of biopolymers have also been studied using mechanical probes such as optical and magnetic tweezers or atomic force microscopes. However, the micron-sized beads or cantilevers that are used preclude microsecond timescales because their dynamics is slowed by hydrodynamic drag.

Embodiments of the present invention use a plasmonic two-particle system to measure the conformational dynamics of a single interconnecting molecule on microsecond timescales and in real-time. A conformational change of the interconnecting molecule will modulate the interparticle distance and will result in a shift of the plasmon resonance of the dimer. This approach enables microsecond time resolution.

Dimers of plasmonic nanospheres have been employed to measure the presence of analyte in a biosensing assay. However, plasmon shifts of a gold-sphere dimer cannot be monitored with microsecond integration times due to their broad plasmon resonance and their relatively low optical cross section per unit volume. Instead of a dimer of nanospheres, preferred embodiments of the present invention use a dimer composed of a gold nanorod and a gold nanosphere. A rod-sphere dimer has two key advantages over previous approaches:

1. Microsecond integration times: The nanorod's optical response is narrow, bright and not easily saturated. This enables us to probe plasmon shifts with microsecond integration times, which we will use to study the transition path time of a single molecule that folds in real-time. 2. Observation times of hours: The optical response of a plasmonic particle does not blink or bleach, enabling observation times that are only limited by the stability of the microscope. We will use this capability to probe many subsequent transition paths of the same molecule and study the degree of heterogeneity of the folding transition.

Similar to riboswitches, these aptamers exhibit a compact conformation when a target is bound. Importantly, aptamers are commercially available with a range of functional groups to allow for conjugation to an optical probe.

A plasmonic dimer according to a preferred embodiment includes a colloidal gold nanorod. They have a 3-5 fold reduction in line width compared to their spherical counterparts. Moreover, their optical cross sections and their plasmon shift in response to nearby metal particles are more than ten times larger compared to a sphere of equal volume. In embodiments of the present invention, these nanorods are used to probe microsecond conformational dynamics of a single aptamer.

Figure 3:
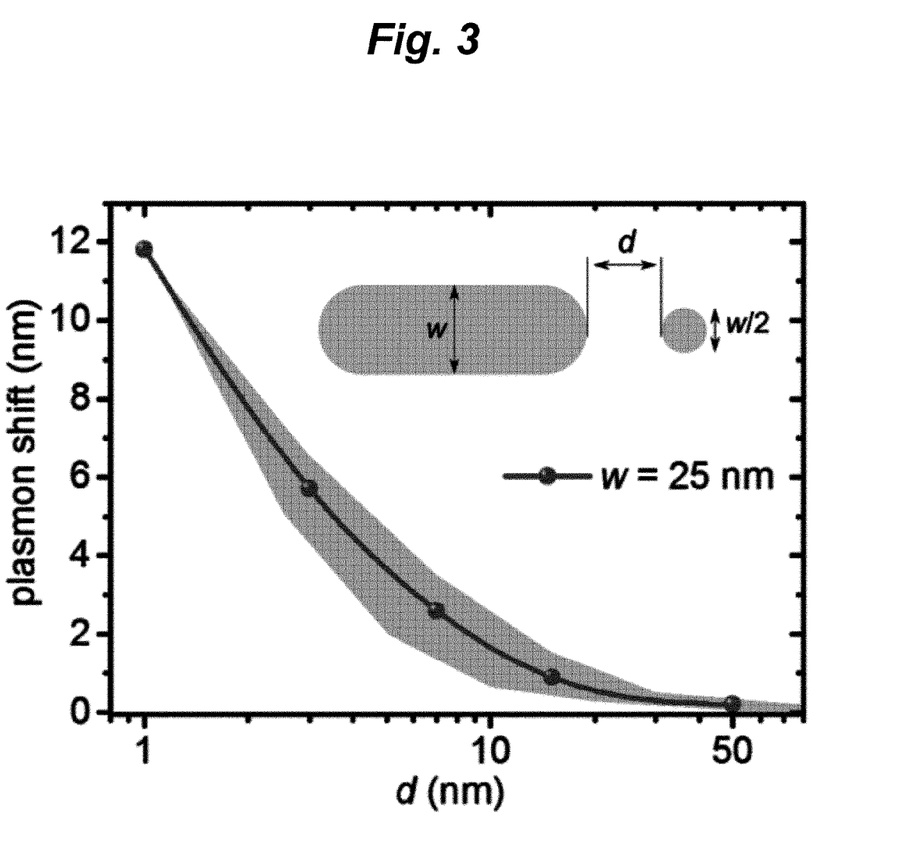
FIG. 3 is a graph of plasmon shift vs. separation distance for a rod-sphere dimer in water, according to an embodiment of the present invention.

In a preferred embodiment, an aptamer is labeled with a small spherical gold particle at one end, while the other end is attached to the gold nanorod (FIGS. 1A-B). Conformational changes of the aptamer modulate the position of the spherical particle in the decaying field of the nanorod, leading to a shift of the dimer's plasmon resonance. The significant plasmon shifts depends on the decay length of the field around the tips of the particle, which can be varied by employing nanorods with different sizes (wet-chemical synthesis protocols allow control over the width of the fabricated nanorod between 10 nm and 40 nm). The plasmon wavelength peak of the rod-sphere dimer then exhibits sensitivity to conformational changes that range from a few nanometers to a few tens of nanometers, as shown in the graph of FIG. 3, which shows a numerical calculation (discrete dipole approximation) of the plasmon shift for a rod-sphere dimer in water as a function of spacing for a 25 nm wide nanorod and 12.5 nm wide nanosphere. The shaded region indicates the range of shifts for 10 nm to 40 nm wide nanorods. These length-scales are comparable to the size of many biomolecules including short oligonucleotides such as aptamers. Importantly, the long range over which plasmon shifts are obtained allow incorporation of spacers of a few nanometers between the aptamer and the particles to reduce steric effects that might affect the conformational dynamics. For such a rod-sphere dimer as shown in FIG. 3 a time-averaged plasmon shift is approximately 5 nm.

In contrast to approaches based on organic fluorophores, the brightness of the scattered signal using plasmon resonance detection allows analog detection (in contrast to photon counting) and continuous microsecond integration times with high signal-to-noise ratios (S/N). Plasmon shifts may be measured by detecting the scattered signal using a fast silicon photodiode. To achieve a strong scattering signal against a low background, one embodiment of the invention uses total-internal-reflection excitation using a laser source. A shift of the plasmon resonance induces a subsequent change in the scattered intensity (typically a 20% signal change is observed for a 5 nm shift when the laser wavelength is on the wing of the plasmon). This allows detection of 5 nm plasmon shifts in 1 µs with S/N more than 10 for nanorods with an aspect ratio of 3 and a width greater than 25 nm. These integration times allows clear resolving of the transition path of single aptamers on timescales of 10-100 µs.

The timescales not only depend on the optical properties of the plasmonic particles but also on the hydrodynamic drag of the tethered gold sphere. Based on its diffusion coefficient, however, a 12.5 nm diameter gold sphere is estimated to take about 3 µs to move over a distance of 10 nm (the typical length-scale of the conformational change). This timescale is shorter than the transition path time and will therefore not significantly perturb the measurement.

The microsecond time-resolution of this plasmonic measurement technique allows one to directly resolve the transition between two states. Importantly, the photostability of the plasmon resonance uniquely allows one to perform statistics on subsequent events on the same molecule. This enables the study the heterogeneity of the transition path time.

Figure 4:
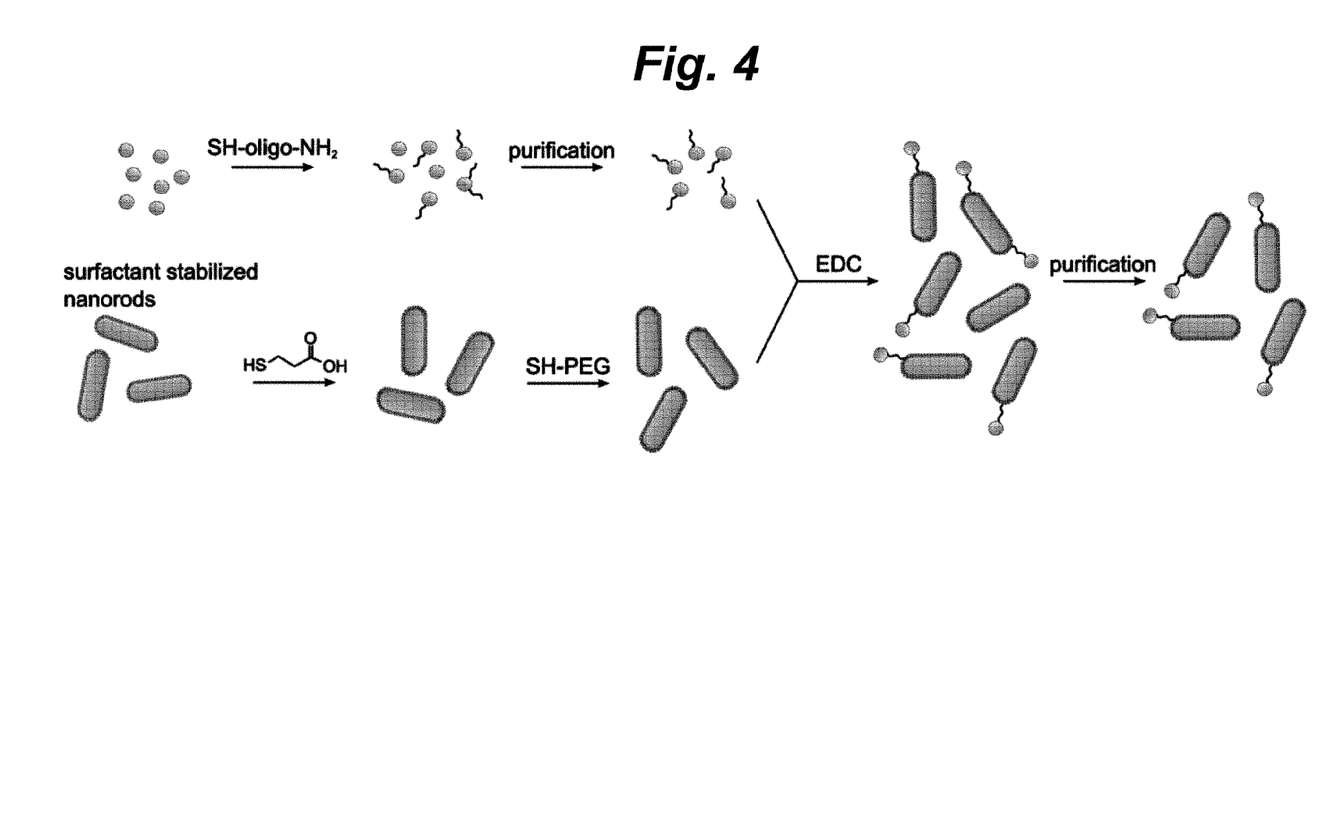
FIG. 4 is a schematic overview of a possible pathway for the preparation of a rod-sphere dimer bridged by an oligonucleotide, according to an embodiment of the present invention.

FIG. 4 is an overview of one possible pathway for the preparation of the rod-sphere dimer bridged by an oligonucleotide. Solution-phase protocols are used to assemble dimers of gold nanoparticles using thiolated oligonucleotides. This is combined with protocols to specifically functionalize the tips of gold nanorods, allowing precisely one oligonucleotide to be conjugated to the tip of a nanorod, where the field-enhancement is highest.

Figure 5:
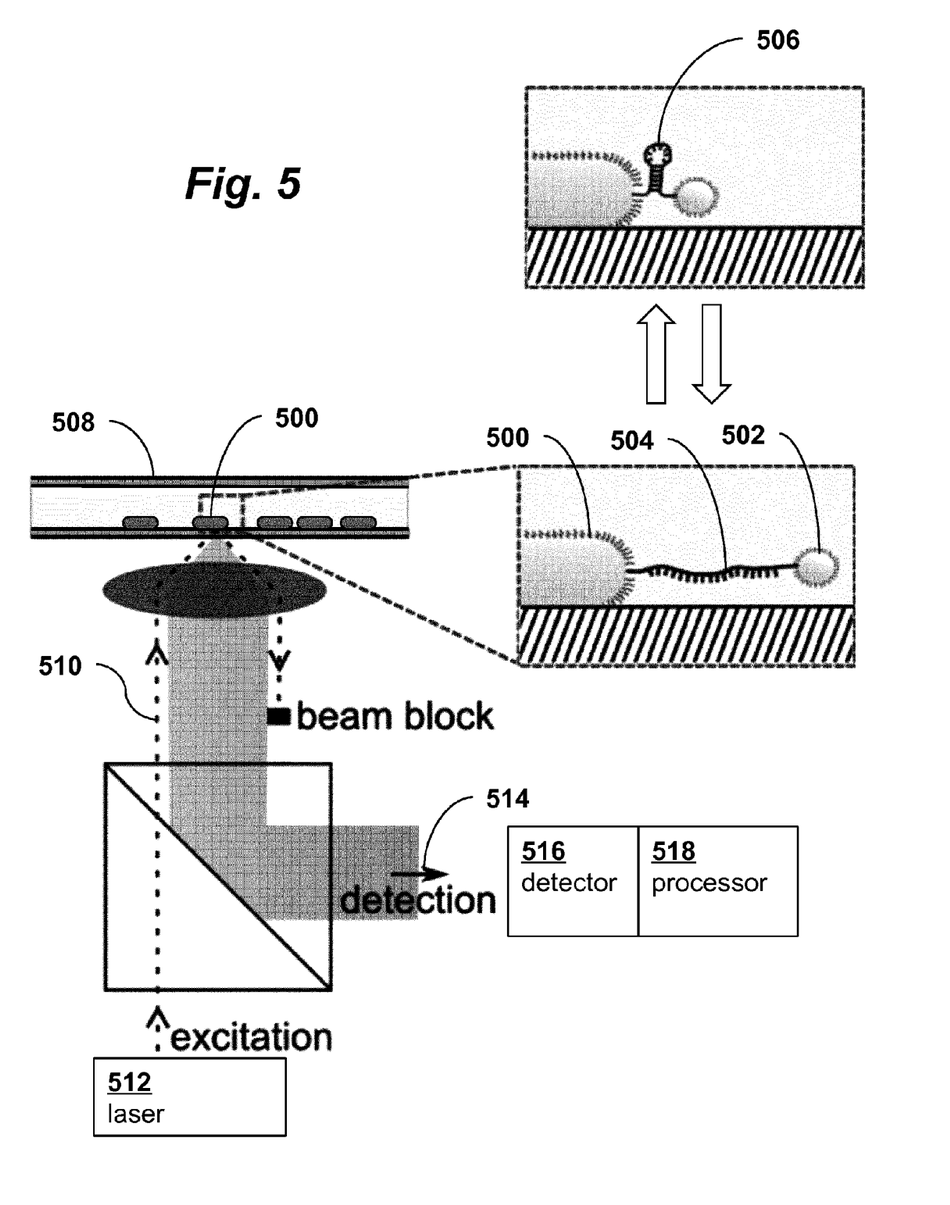
FIG. 5 is a schematic diagram of a system for sensing the presence of a target analyte using optical excitation and detection of plasmon resonance shifts in dimers, according to an embodiment of the present invention.

FIG. 5 is a schematic diagram illustrating a technique for optical excitation and detection of plasmon resonance shifts in dimers composed of a nanorod 500 and nanosphere 502 connected by single-stranded DNA oligonucleotide 504 that is selected to fold into a hairpin structure 506 in the presence of a target analyte. The rod-sphere dimers are immobilized onto coverslips in a flow-cell 108. An illumination beam 510 from a laser 512 undergoes total-internal-reflection in the wall of cell 508 and excites plasmons in the single rod-sphere dimer. An optical scattering signal 514 of the dimer is directed to an optical detector 516, where it appears against a dark background, ensuring a high signal-to-noise ratio. Plasmon shifts will then result in changes of detected signal intensity. A processor 518 analyzes signals from detector 516 to determine the presence of target analyte.

The detector 516 may be an electron multiplying charge-coupled-device (EM-CCD) which can image many individual dimers simultaneously. Alternatively, to reach microsecond integration times, the scattered intensity of a single rod-sphere dimer may be projected onto an analog photodiode. Varying the number of base pairs in the DNA hairpin stem allows tuning the transition path time between 10 and 100 µs.

The technique of using a plasmonic dimer to probe conformational changes in biomolecules to sense analytes gives access to observation times of hours while simultaneously allowing for microsecond integration times.

The biomolecules may include proteins, where site-specific labeling can be achieved using, e.g., protein engineering.

The analyte biosensing technique allows for the sensitive detection of extremely small targets because the signal relies on a conformational change of the aptamer that is amplified by the presence of the gold nanosphere. It has significant sensitivity by allowing for single-molecule detection. The selectivity is significantly higher than ensemble-averaged methods because single-molecule resolution allows for the discrimination between specific (strong, long-lived) and non-specific (weak, short-lived) interactions on a per-molecule basis. Broad applicability is warranted because aptamers can in principle be selected against any target. Aptamers against drugs, peptides, amino acids, metal ions and metabolites are already commercially available.

Embodiments of the present invention may use techniques of dark field scattering spectroscopy. Specifically, it may use techniques using a bright low-temporal coherence light source, preferably with a linewidth larger than 5 nm (e.g., superluminescent diode) for dynamically measuring changes in the plasmon resonance peak of plasmonic particles.

Most detection methods for scattering objects such as metallic nanoparticles use dark-field illumination to obtain an image in which the object has a higher intensity than the background. For small particles (<100 nm in diameter for gold) the scattering signal reduces as the sixth power of the radius and quickly becomes swamped by the background. Imaging smaller objects therefore requires a high irradiance to obtain enough signal.

Imaging and/or spectroscopy of scattering objects is usually performed with a non-coherent white-light source (emission bandwidth >1000 nm). It allows for the imaging of scattering objects against a homogeneous and low background, and it can be used to extract a broadband scattering spectrum by determining the scattering signal at many different wavelengths using the same illuminator. Commonly employed sources are incandescent lamps (e.g., halogen) or arc-discharge sources (e.g., Xenon). The main disadvantage of these sources is their extended emitting area (>1 mm$^2$), which does not permit tight focusing of the beam to achieve a high irradiance of the sample.

One way to overcome this is by using a narrowband and coherent light source such as a laser. The high coherence and low bandwidth (typically <1 nm) allow for the tight focusing of the beam to achieve a high irradiance of the sample. However, coherent laser irradiation has limitations because (1) interference fringes cause an inhomogeneous illumination pattern and (2) small spurious reflections and leakage of light in the optical setup cause background artefacts in the image. Such artefacts significantly reduce the signal-to-noise ratio and may fluctuate in time due to vibrations and thermal drifts of the optical setup.

In such biosensing applications white-light sources or lasers are known to be useful to measure spectral shifts. White-light sources exhibit a spectral breadth B much larger than the line width $\Gamma$ of a nanoparticle (i.e., B>>$\Gamma$), and thus allows for the measurement of the whole spectrum at once using a spectrometer. Shifts of the spectrum are then extracted by analyzing subsequent spectra. On the other hand, spectral shifts are also measured using a source that is much narrower than the line width of the particle, e.g., a laser (B<<$\Gamma$). The time-dependent scattered signal will change when the spectrum of the object shifts. However, because superluminescent diodes (SLDs) exhibit a spectral breadth that is similar to the line width of nanoparticles (i.e. B~$\Gamma$), the use of SLDs for dynamic spectral shift measurements on nanoparticles is unexpected. Optical coherence tomography also uses SLDs for illumination, but there is no intention to measure spectral changes of the sample. Although particles with different plasmon resonances are used, the resonance wavelength is fixed and does not change in time. Thus, the measurement of dynamic behavior of plasmons using an SLD is unexpected because it is not intuitive to choose for a light-source that has a bandwidth only slightly narrower than the line width of the resonance that is probed.

The line width of a metal nanoparticle is typically 40-50 nm. A white-light source such as a halogen lamp has a line width much broader than a nanoparticle. A laser has a line width much narrower than a nanoparticle, whereas the line width of a typical SLD is typically 15-30 nm, depending on the emission wavelength, which is comparable to the line width of a nanoparticle.

Figure 6A:
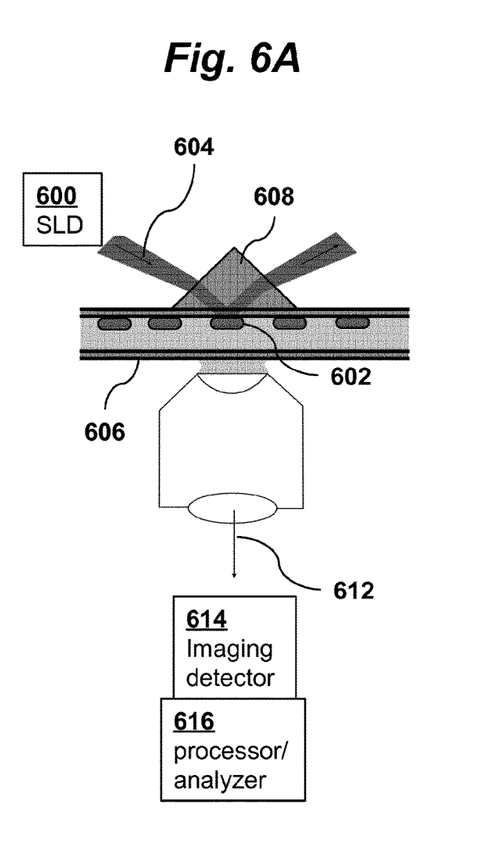
FIGS. 6A-B illustrate two implementations of a combined microscopy and spectroscopy method, according to embodiments of the present invention.
Figure 6B:
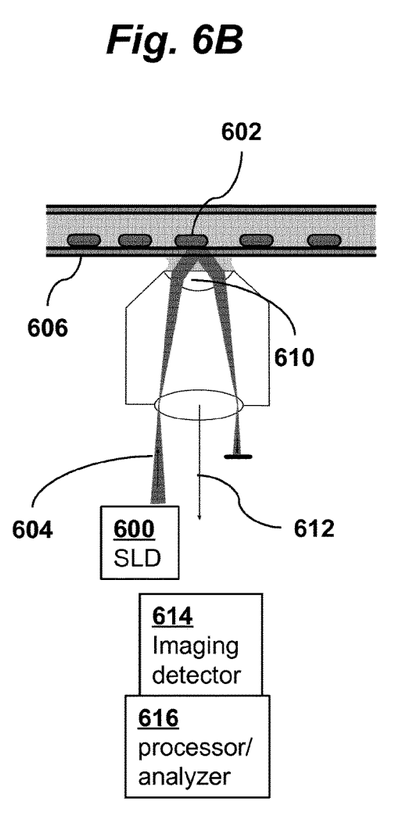

FIGS. 6A-B illustrate two implementations of a combined microscopy and spectroscopy method that use a bright and low-coherence light source, a superluminescent diode (SLD) 600, for the time-dependent imaging of scattering objects 602. In the biosensing techniques of embodiments of the present invention, the time-dependent signal represents shifts of the plasmon resonance peak of the scattering object indicative of the presence of an analyte. The shorter coherence length of the SLD light 604 compared to laser light significantly reduces the artefacts caused by interference, while the brightness of SLDs is similar to common diode lasers.

The low coherence and intermediate bandwidth (e.g., 15-30 nm at near-infrared wavelengths) of the beam result in homogeneous illumination and low background intensity. The high brightness and small emitting area (e.g., <30 µm$^2$ when coupled to a single-mode fiber) ensure a high irradiance. The scattering signal from an object illuminated with a superluminescent diode is high compared to the background and stable on short as well as long timescales.

In FIG. 6A the SLD 600 illuminates the sample 602 under an angle exceeding the angle for total internal reflection at a glass-water interface of a liquid cell 606. In this implementation, the light 604 is coupled to the sample 602 via a glass prism 608. In an alternate implementation, shown in FIG. 6B, the light 604 is coupled to the sample 602 via the back aperture of an objective lens 610. Because the implementation in FIG. 6A separates the excitation and emission light-paths, it leads to a lower background and higher signal-to-noise ratio than the implementation in FIG. 6B. The implementation in FIG. 6B may be useful if the space above the sample is to be used for other purposes, e.g., a technical component for temperature regulation. In both implementations, because the angle of illumination is higher than the angle for total-internal-reflection at the glass-water interface of the cell 606, all the excitation light is reflected. The presence of the particle 602 perturbs the total-internal-reflection, leading to a certain intensity of scattered light 612 that is partly collected by the objective and sent to an imaging sensor 614. The reflected beam is blocked by a beam-block, and the remaining scattered light is sent to an imaging detector 614, preferably a camera with sufficient dynamic range and wavelength sensitivity to achieve single-molecule resolution. In another embodiment, the sample 602 can be mounted on an optical probe (e.g., optical fibre) to allow for measurements to be conducted directly in complex biological environments. Signals from detector 614 are then analyzed by a processor 616 to determine the presence of the target analyte.

The assay may involve e.g., a binding assay, a competitive assay, a displacement assay, a sandwich assay, an enzymatic assay, an assay with target and/or signal amplification, a multi-step assay, an assay with molecular cascade, etc. The assay may involve recognition moieties of different natures, e.g., peptides, proteins, nucleic acids, carbohydrates, etc. Embodiments may include various calibration methods, controls, multiplexing, etc. Embodiments may include measures to block and reduce unwanted processes (e.g., non-specific processes that generate background signals) and to increase efficiency, stability, and selectivity of signal generation.

Embodiments of the present invention include a system and technique for biosensing an analyte in a matrix using a large collection of nanoscale detectors whose optical properties are individually altered in the presence of an analyte. In preferred embodiments, for example, a plasmonic biosensor based on hundreds of individual gold nanorods with single-molecule sensitivity are simultaneously monitored in real-time within a dark-field microscopy setup.

We present a plasmonic biosensor based on hundreds of individual gold nanorods with single-molecule sensitivity that are simultaneously monitored in real-time within a dark-field microscopy setup. The approach allows for the statistical analysis of single-molecule interactions without requiring any labeling of the analyte. We study an antibody-antigen interaction and find that the waiting-time distribution is concentration-dependent and obeys Poisson statistics. The ability to probe hundreds of nanoparticles simultaneously will provide a sensor with a dynamic range of 7 decades in concentration and will enable the study of heterogeneity in molecular interactions.

Single-molecule detection has distinct advantages over ensemble-averaged techniques because it yields statistical distributions of molecular properties instead of averages, and reveals rare and unsynchronized events. Preferred embodiments of the invention include techniques for monitoring hundreds of single-molecule plasmonic sensors in real-time using total-internal-reflection excitation in a standard microscope. The waiting-time distribution of an antibody-antigen interaction obeys Poisson statistics and is concentration dependent. The parallelized detection provides a dynamic range of 7 decades in concentration.

In one implementation of the embodiments shown in FIGS. 6A-B, the superluminescent diode is a Superlum, with center wavelength 795 nm, bandwidth 14 nm, maximum power 35 mW. The detector 614 is a charge coupled device (CCD), e.g., with an area of 50×50 $\mu m^2$ on the sample surface.

The density of particles on the substrate may be controlled by the concentration during spin coating to yield 150-250 particles in a 100×100 $\mu m^2$ field-of-view of the microscope. Each particle site exhibits a different scattered intensity caused by (a) the inevitable dispersion in particle volume and aspect ratio leading to a different scattering cross-section at the irradiation wavelength, and (b) a different orientation of each particle in the partly polarized evanescent field. To ensure that the technique probes single nanorods, white-light scattering spectra of all the particles are recorded. Less than 10% of the particles are in clusters, which are discarded in the analysis.

The use of a superluminescent diode (SLD) as the light-source is important to achieve sufficient signal-to-noise ratio (S/N). The poor spatial coherence of light from an incandescent lamp provided insufficient intensity to image the small particles, whereas the high temporal coherence of laser illumination resulted in interference artifacts that induce signal fluctuations. SLD's are semiconductor high-gain devices that generate amplified spontaneous emission. In this application the low temporal coherence of the SLD significantly reduced interference artifacts whereas the high spatial coherence ensured a high illumination intensity. This resulted in shot-noise limited signals for an integration time of 100 ms.

In a typical single-molecule experiment an analyte is passed into the flow cell using a syringe pump. The CCD camera is used to record the time-dependent scattered signal (determined by a two-dimensional Gaussian fit of each spot in each frame). Plasmon shifts caused by biomolecular binding are then observed as step-wise changes in the normalized scattered intensity as a function of time using a step finding algorithm. Stepwise changes in the signal indicate stochastic binding of single antibodies (antibody concentration 10 nM). The sign of the stepwise changes depends on the plasmon wavelength relative to the wavelength of the irradiation source. The magnitude of the steps varies from 1% to 5%, with the variation of step-sizes indicating differences of position and orientation. The sign of the signal caused by analyte binding depends on the plasmon wavelength relative to the SLD wavelength. For particles with a plasmon wavelength shorter than the SLD wavelength the red-shift of the plasmon causes an increase in the scattered signal, whereas particles with a plasmon wavelength longer than the SLD wavelength exhibit the opposite behavior. A fraction of the particles does not exhibit step-wise changes of the signal because the plasmon wavelength is close to the SLD wavelength. For that reason the analysis may exclude particles with a plasmon resonance between 775 nm and 815 nm. It may also exclude steps with a S/N<2 (defined as the ratio between step-size and standard-deviation of the signal before analyte injection) which we attribute to drift of the background or analytes binding to the glass surface close to the particles.

Figure 7:
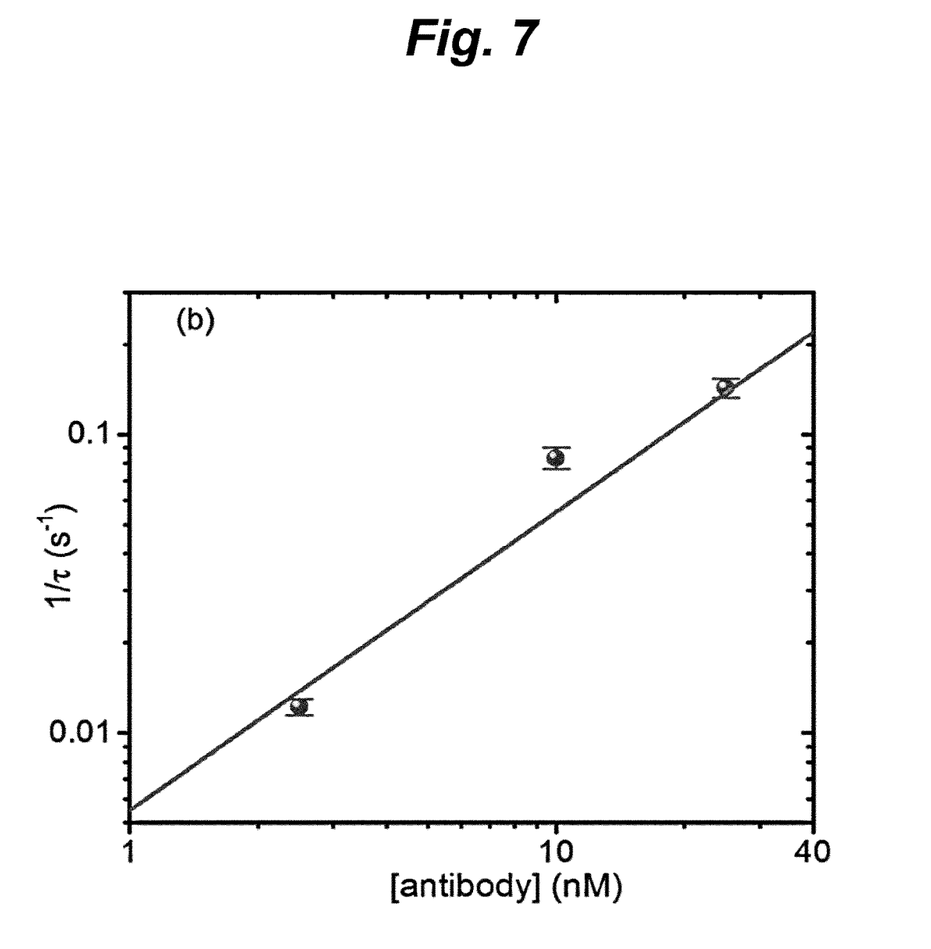
FIG. 7 is a graph of mean binding rate vs. analyte concentration according to a power law, according to an embodiment of the present invention.

From the step finding fit to the data the processor can estimate a value for $\tau$, the mean waiting-time between steps. The distribution of waiting-times obeys Poisson statistics, with a mean binding rate that depends on the analyte concentration according to a power law, as shown in the graph of FIG. 7.

The detected scattered intensity is obtained by fitting a particle's diffraction-limited spot in each frame with a two-dimensional Gaussian. The S/N (defined as the ratio between the mean and the standard-deviation of the signal over 150 seconds) increases for brighter particles. The S/N approaches the shot noise limit with some excess noise that is likely caused by fluctuations of the SLD intensity and slight mechanical drift of the sample. From these measurements we conclude that step-wise signal-changes of 1% can be detected with a S/N of 3-5 for particles with an integrated intensity over $10^5$ cnts/s.

The precision with which an analyte concentration can be determined is limited by counting statistics. For example, at least 100 molecules need to be detected in a defined time window in order to have a precision of concentration-determination of about $1/\sqrt{100}=10\%$. Small particles have a limited number of receptor molecules on their surface, so an individual particle can capture only a limited number of analyte molecules. Furthermore, in the limit of very low analyte concentration, there is a high probability that a single particle will not have captured even a single analyte molecule, even for long incubation times. To address this issue, a biosensing system according to preferred embodiments of the invention have at least 100 dimer particles, and time traces are recorded on the individual particles. The data of the particles is combined by the processor in order to determine an analyte concentration. For low analyte concentration, preferably data is combined from at least 1000 particles, more preferably at least 10,000 particles.

Due to variations during the fabrication process of the nanoparticles, they may have variable distinct sizes, resulting in inconsistent spectral properties. To address this issue, it is preferable to use particles with an inherently narrow distribution of plasmon resonances, e.g., gold bipyramids.

The inventors have found that the ensemble line-width of the extinction spectrum of a solution of bipyramids approaches the single-particle line width of 50 nm, whereas the ensemble line width of gold nanorods is typically ~200 nm. This indicates that the individual bipyramids are optically more homogeneous. To address this issue it is also preferable to use a biosensing system with multiple wavelengths. A preferred solution is to record time-traces at a number of different wavelengths, e.g., using a wavelength-tunable superluminescent diode.

It is advantageous to have a biosensing system with a high number of particles. However, in a miniaturized system only a limited surface area is available. Furthermore, the density of particles on the surface is limited, because the optical system needs to be able to record time traces of individual objects. To address this issue, it is preferable to have system in which more than a predetermined fraction of the particles are separated from nearest-neighbor particles by at least the diffraction limit of the optical system. Another way to address this issue is to use an ordered pattern of particles on the surface, rather than a random distribution. Preferably the pattern of particles on the surface is conformal to the pattern of pixels on a digital camera chip. Digital cameras typically have rectangular pixels; for a camera chip with rectangular pixels, the particles are preferably situated on a rectangular grid. Another way to address this issue is to use an optical system in which a single particle maps onto a single pixel of a digital camera chip. Preferably, a single particle gives a signal on a single pixel that is at least 5 times higher than the signal on that pixel caused by neighbouring particles. Another way to address this issue is to use particles with different spectral properties, patterned in an alternating way on a surface, with a minimal spacing below the diffraction limit. Due to the different spectral properties, sub-populations of particles can be selected and time-traces can be recorded on different sub-populations with single-particle resolution, even if they are spaced by less than the diffraction length.

In a particle-based biosensing technology with optical detection and single-particle resolution, it is important to identify and ignore undesired particle-like objects that are sources of noise. Particle-like objects of this kind may be related to sample contamination or aggregates in the sample, or because of biochemical properties of sensing particles (e.g., surface functionalization), particle properties (e.g., shape, optical properties), or configurations of particles with other particles (e.g., multi-particle aggregate, or multiple particles in proximity that cannot be optically resolved). To address this issue, spectral properties of these particles can be recorded and compared to reference data. The spectral properties can be recorded, e.g., using a broadband light source and tunable filter, or using a source with tunable wavelength. Spectral signals can be used to identify unreliable objects caused e.g., by particle properties (e.g., shape) or particle configuration (e.g., clusters of particles). Individual nanorods are characterized by a single narrow Lorentzian spectrum, allowing us to discard clusters based on the line shape and line width of the spectrum. Also, the scattering spectrum of clusters of nanoparticles exhibit a double peak or no clear peak at all. These clusters can easily be distinguished from the spectra of individual particles and are discarded from the data analysis.

Another technique to address this issue is to compare signal time-traces of individual objects with time-traces of a plurality of other objects. Objects having characteristics that strongly deviate from a plurality of other objects may be rejected, e.g., based on noise characteristics, drift, step sizes, number of steps, cumulative signal over a long time, etc.

The dynamic range of the sensor has low- and high concentration limits. Low analyte concentrations limit the statistics because the binding rate is low. For low concentrations, the minimum accessible concentration is determined by the number of particles in a field-of-view. The 2D Gaussian fitting algorithm currently requires a region-of-interest of 10×10 pixels to obtain an accurate fit for a magnification of 60×. High-end scientific cameras having a resolution of over 5 megapixels have an estimated number of particles of 50 in the field-of-view under optimum conditions. The lowest accessible concentration is then $c \approx 0.5$ pM. Higher analyte concentrations exhibit an increased rate of binding, for which a higher frame rate (i.e., a shorter integration time) is required to resolve all single-molecule binding events. Based on the Poisson distributed waiting times, a frame rate of $50/\tau$ will ensure that the short times in the distribution are also resolved. By increasing the incident intensity from 64 W/cm$^2$ to 1 kW/cm$^2$ the integration time is reduced to 6 ms with only a modest reduction in S/N. The maximum frame rate that can be achieved is fundamentally limited by the photo-thermal heating of the nanoparticles. For studies on biological samples the maximum permissible temperature rise is of the order of 10 K, which we estimate is reached for an incident intensity of 10 kW/m$^2$. This implies that a frame rate of 20 fps is achievable without inducing thermal damage to the analyte. Such high frame rates give access to low-affinity interactions or to analyte concentrations as high as about 5 μM.

Probes for biosensing with single-molecule resolution (e.g., a metal nanoparticle, a dielectric resonator, a solid-state nanopore) typically exhibit a limited dynamic range due to the low number of binding sites per probe, prohibiting the accumulation of sufficient statistics at low analyte concentrations. This limitation is overcome in embodiments of the present invention by the parallelized probing of many sensors, giving an extraordinary projected dynamic range of 7 decades in concentration. The ability to extract distributions of molecular interaction parameters enables the investigation of heterogeneity in a population of unlabeled molecules. The simple and cheap optical layout allows the sensor to be implemented easily with a microscope.

High analyte concentrations will give binding events with a high rate of binding. This makes it complicated to resolve individual binding events in measured time-traces. Also, low-affinity interactions can give rise to short-lived states which are difficult to resolve. To address this issue, it is preferable to use an optical system with a high frame rate. Preferably the frame rate or reciprocal integration time is higher than 100 s$^{-1}$, more preferably higher than 1000 s$^{-1}$.

The temperature of the particles is crucial because the structure and activity of the protein can be impaired when it is heated for extended periods of time. Most globular proteins exhibit a melting temperature ranging from 40.0 to 80.0 depending on pH and buffer conditions. Based on a theoretical model, it is estimated that an incident intensity exceeding 10 kWcm$^{-2}$ is needed to raise the particle temperature by more than 10 K.

A high signal-to-noise ratio and high frame rate can be achieved using a light source with high power. However, a high optical power can give an unacceptable temperature rise in the sample fluid, thereby affecting the biochemical materials. To monitor this potential issue, an optical thermometer may be integrated with the system. For example, using a phase-sensitive camera, or monitoring the blueshifted emission from the metallic particles, may be implemented. To maintain an acceptable temperature the incident power can be adjusted.

A drift of optical signal from the particles due to binding and unbinding events complicates the observation of signals. To address this issue, it is preferable to use an internal reference to continuously or periodically calibrate the optical signal, e.g., a particle or another fiducial object with optical activity on the surface, which gives a stable optical scattering signal, without resonant properties and without sensitivity to molecular binding. The signal from a reference particle will be an optical reference for the illumination and detection status of the system. The reference signal can be used by the processor to correct for fluctuations in the optical signals from the biosensing particles, caused by drift in the components of the optical system and fluctuations of the intensity of the light source. The use of multiple reference particles on the surface will further improve the calibration. Examples of reference or fiducial markers are polystyrene spheres, nanopatterned surface structures, PDMS islands. Optical signal fluctuations can be caused by changes of optical path length, e.g., perpendicular to the imaging plane (z-axis). To address this issue, it is preferable to have an active z-axis feedback and control in the system.

Analyte multiplexing, i.e., measurement of different analytes at the same time, is advantageous for increased biomedical sensitivity and specificity. To provide for such multiplexing, some embodiments use particles that have different receptors on their surface. For reasons of counting statistics and precision, the number of particles should be at least equal to 100 for every analyte, and higher when necessary for an analyte with a low binding event rate (e.g., because it has a low concentration, or due to the affinity and density of the receptors). The minimal frame rate of the optical system is determined by the analyte with the highest (un)binding event rate. Also, some embodiments use particles with different optical properties, so that the different particles can be mixed. The particles preferably have at least two sub-populations that can be optically distinguished and that have different receptors on their surface. Also in this case, for reasons of counting statistics and precision, the number of particles is preferably at least 100 for every analyte, and higher for an analyte with a low binding event rate (e.g., because it has a low concentration, or due to the affinity and density of the receptors). The minimal frame rate of the optical system is determined by the analyte with the highest event rate.

The features described in various separate embodiments of the invention are not necessarily exclusive and, in general, may be used in combination with each other. Such features and embodiments also include material disclosed in U.S. provisional patent applications 62/078,870 filed Nov. 12, 2014, 62/092,763 filed Dec. 16, 2014, and 62/132,096 filed Mar. 12, 2015, all of which are incorporated herein by reference.

The invention claimed is:

1. A method for sensing an analyte, the method comprising:
    bringing a matrix containing the analyte into contact with a sensor device having protrusions containing free charge carriers, where conformational molecules are bound at a first end to the protrusions, and bound at a second end to a particle label, where the particle label and protrusion can move with respect to each other, where the conformational molecule changes its conformation when bound to the analyte, thereby changing the distance and/or the relative orientation of the particle label to the protrusion; where the protrusions have a long axis that is smaller than 200 nm, and at least one short axis that has a length that is shorter than 80% of the long axis;
    exciting free charge carriers in the protrusions;
    detecting optical radiation from the protrusions;
    wherein the exciting and/or detecting is performed at a wavelength near a plasmon resonance of the protrusion while the matrix containing the analyte is in contact with the protrusions of the sensor device;
    determining the presence/concentration of the analyte from changes in the detected optical radiation while the matrix containing the analyte is in contact with the protrusions of the sensor device.

2. The method of claim 1 wherein bringing the analyte into contact with the protrusions of the sensor device comprises bringing a fluid containing the analyte or an analyte-permeable matrix containing the analyte into contact with the protrusions of the sensor device.

3. The method of claim 1 wherein the protrusions are non-spherical metallic particles, nanorods, bipyramids, nanostars, platonic nanoparticles.

4. The method of claim 1 wherein the particle label has an electrical polarizability different than a spatial or time-average polarizability of the matrix.

5. The method of claim 1 wherein exciting free charge carriers in the protrusion near a plasmon resonance comprises exciting the free charge carriers by exposing the protrusion to optical or electrical energy.

6. The method of claim 1 wherein exciting free charge carriers in the protrusion near a plasmon resonance comprises exciting the free charge carriers by exposing the protrusion to optical light from a light source with a linewidth larger than 5 nm or a superluminescent diode.

7. The method of claim 1 wherein detecting optical radiation near the plasmon resonance wavelength of the protrusion comprises detecting optical radiation within five times the full width half maximum of a plasmon resonance wavelength peak.

8. The method of claim 1 wherein determining the presence/concentration of the analyte comprises performing histogram and/or histogram processing to suppress background noise and enhance specificity.

9. A sensor device for sensing an analyte, the sensor device comprising:
    protrusions from a surface of the sensor device, wherein the protrusions contain free charge carriers; where the protrusions have a long axis that is smaller than 200 nm, and at least one short axis that has a length that is shorter than 80% of the long axis; where the protrusions are non-spherical metallic particles, nanorods, bipyramids, nanostars, or platonic nanoparticles;
    particle labels;
    conformational molecules, each being bound at a first end to one of the protrusions, and bound at a second end to one of the particle labels, where the one of the particle labels and the one of the protrusions can move with respect to each other, where each of the conformational molecules changes its conformation when bound to the analyte, thereby changing the distance and/or the relative orientation of the one of the particle labels to the one of the protrusions;
    means for exciting free charge carriers in the protrusions;
    means for detecting optical radiation from the protrusions;
    wherein the exciting and/or detecting is performed at a wavelength near a plasmon resonance of the protrusion;

means for determining the presence/concentration of the analyte from changes in the detected optical radiation.

* * * * *